(12) United States Patent
Sai et al.

(10) Patent No.: US 12,078,606 B2
(45) Date of Patent: Sep. 3, 2024

(54) GAS SENSOR

(71) Applicants: Figaro Engineering Inc., Minoo (JP); University of Fukui, Fukui (JP)

(72) Inventors: Masakazu Sai, Minoo (JP); Kenichi Yoshioka, Minoo (JP); Kuniyuki Izawa, Minoo (JP); Toshikazu Sakaguchi, Fukui (JP)

(73) Assignees: FIGARO ENGINEERING INC., Osaka (JP); UNIVERSITY OF FUKUI, Fukui (JP)

( * ) Notice: Subject to any disclaimer, the term of this patent is extended or adjusted under 35 U.S.C. 154(b) by 449 days.

(21) Appl. No.: 17/432,973

(22) PCT Filed: Mar. 17, 2020

(86) PCT No.: PCT/JP2020/011690
§ 371 (c)(1),
(2) Date: Aug. 23, 2021

(87) PCT Pub. No.: WO2020/189675
PCT Pub. Date: Sep. 24, 2020

(65) Prior Publication Data
US 2022/0163474 A1 May 26, 2022

(30) Foreign Application Priority Data
Mar. 19, 2019 (JP) ................. 2019-050582

(51) Int. Cl.
*G01N 27/12* (2006.01)
*B01D 53/22* (2006.01)
(Continued)

(52) U.S. Cl.
CPC ........ *G01N 27/128* (2013.01); *B01D 53/228* (2013.01); *B01D 53/229* (2013.01);
(Continued)

(58) Field of Classification Search
CPC .................... G01N 27/126; G01N 27/128
See application file for complete search history.

(56) References Cited

U.S. PATENT DOCUMENTS 4,354,913 A * 10/1982 Pungor .................. C12Q 1/002
204/403.08
5,338,430 A * 8/1994 Parsonage .......... G01N 27/4045
204/414
(Continued)

FOREIGN PATENT DOCUMENTS

JP 59-221971 A 12/1984
JP 2013-242269 A 12/2013
(Continued)

OTHER PUBLICATIONS

Official Communication issued in International Patent Application No. PCT/JP2020/011690, mailed on Jun. 23, 2020.
(Continued)

*Primary Examiner* — Jamel E Williams
*Assistant Examiner* — Alex T Devito
(74) *Attorney, Agent, or Firm* — Keating & Bennett, LLP

(57) ABSTRACT

A gas sensor comprises a gas separation membrane comprising substituted polyacetylene where a substituent group is combined to a double-bonded carbon atom in the backbone chain of the substituted polyacetylene and a sensing element configured to detect gas permeated through the gas separation membrane.

8 Claims, 3 Drawing Sheets

(51) Int. Cl.
*B01D 69/02* (2006.01)
*B01D 69/10* (2006.01)
*B01D 71/44* (2006.01)
*G01N 33/00* (2006.01)

(52) U.S. Cl.
CPC ........... B01D 69/02 (2013.01); B01D 69/108 (2022.08); B01D 71/44 (2013.01); G01N 27/126 (2013.01); G01N 33/0047 (2013.01); B01D 2325/20 (2013.01)

(56) References Cited

U.S. PATENT DOCUMENTS

| | | | |
|---|---|---|---|
| 5,407,466 A * | 4/1995 | Lokhandwala | B01D 71/80 95/52 |
| 6,341,629 B1 * | 1/2002 | Clark | B67D 7/342 141/59 |

FOREIGN PATENT DOCUMENTS

| | | |
|---|---|---|
| WO | 2010/104045 A1 | 9/2010 |
| WO | 2010/110051 A1 | 9/2010 |
| WO | 2018/053656 A1 | 3/2018 |

OTHER PUBLICATIONS

Teplyakov et al., "Investigations on the peculiar permeation properties of volatile organic compounds and permanent gases through PTMSP", Journal of Membrane Science, vol. 220, 2003, pp. 165-175.

* cited by examiner

2

22

GAS SENSOR

FIELD OF THE INVENTION

The present invention relates to gas detectors.

BACKGROUND ART

Gas sensors have a problem that catalyst poisons such as cyclo-siloxanes and SOx reduce the gas sensitivity of the gas sensors. Further, they are not enough in the discrimination between gases to be detected and other gases. For solving these problems, adsorbents such as activated charcoal, silica gel, zeolite have been used as filters of gas sensors.

Patent Document 1 (WO2018/053656) has proposed to use gas separation membranes, such as TEFLON AF ("TEFLON AF" is a registered trademark and a product name by DuPont), as filters of gas sensors. These filters work as a sieve according to the sizes of gas molecules, block larger molecules such as cyclo-siloxanes and permeate smaller molecules such as CO, $H_2O$, and ethanol. For maintaining the response speed of gas sensors, TEFLON AF is made into a thin layer of about 1 micrometer thickness on a porous support membrane.

PRIOR DOCUMENTS LIST

Patent Document

Patent Document 1: WO2018/053656

SUMMARY OF THE INVENTION

Problem to be Solved by the Invention

The object of the invention is to provide a gas detector having a novel gas separation membrane.

Means for Solving the Problem

A gas detector according to the invention comprises: a gas separation membrane comprising substituted polyacetylene where a substituent group is combined to a double-bonded carbon atom in the backbone chain of the substituted polyacetylene; and a sensing element configured to detect gas permeated through the gas separation membrane. The gas detector can be a single gas sensor or gas detection equipment comprising a gas sensor, a housing different from the gas sensor, and a peripheral circuit. Regarding a gas sensor, the gas separation membrane is fixed in the housing of the gas sensor, and regarding gas detection equipment, the gas separation membrane is fixed in a gas path or on a gas inlet.

Substituted polyacetylenes include, for example:

poly [1-(trimethylsilyl-1-propyne] (PTMSP), poly [1-(trimethylgermyl-1-propyne] (PTMGP), and similar polymers that include a heteroatom such as Si, Ge, in a substituent group such as "$(CH_3)_3Si-$", "$(CH_3)_3Ge-$";

poly [4-(methyl)-2-pentyene] (PMP), poly [1,2-diphenyl acetylene] (PDPA, and similar polymers that include a large substituent group such as isopropyl group or phenyl group and without a heteroatom;

Poly [1,4,5-$(CF_3)_3$-phenylacetylene], poly [1,5-$(CF_3)_2$-phenylacetylene], and similar polymers that include a large substituent group such as a $CF_3$ group; and poly [1-phenyl-2-[(p-trimethylsilyl) phenyl]acetylene] (PTMSDPA) and similar polymers that include a substituent group such as "$(CH_3)_3Si-$", "$(CH_3)_3Ge-$", and a phenyl group. In particular, PTMSDPA has large size pores due to the p-trimethylsilyl phenyl group and the phenyl group is preferable in the high permeation rate to gases to be detected and the high performance of blocking large cyclo-siloxanes.

Substituted polyacetylene can generally be represented as "-(CA=CB) n-". One of the A, B is a substituent group and the other is hydrogen, or both A and B are substituent groups. In the present specification, a gas separation membrane comprising substituted poly-acetylene means a membrane whose gas permeation property is controlled by substituted polyacetylene in the membrane. Preferably, the principal component (one having the maximal concentration) in the gas separation membrane is a substituted polyacetylene.

Substituted polyacetylenes are rigid due to the double-bonded backbone and have large free volumes due to the large substituent group and the rigid backbone. Further, they have high thermal stability and also chemical stability. Therefore, gas separation membranes comprising substituted polyacetylenes have high gas permeation rates and can permeate large molecules such as toluene. Due to the high gas permeability, relatively thick monolayer membranes of substituted polyacetylenes having a thickness of about 10 to 50 micrometer can be used without reducing the responses to gases, without support layers. Here, monolayer membranes are generally formed more easily than laminated membranes. By the way, a substituted polyacetylene layer laminated on a porous support layer can improve the gas response of gas sensors.

Substituted polyacetylenes permeate large molecules such as isobutane, and toluene. Since it permeates isobutane, it can be used in the detection of LPG. Since it permeates toluene, it can be used in the detection of VOC. Since cyclo-siloxanes are significantly larger than toluene, substituted polyacetylenes do not substantially permeate cyclo-siloxanes. Therefore, it can prevent the poisoning of gas sensors.

Preferably, the sensing element comprises a MEMS chip supporting a metal oxide semiconductor membrane whose resistance changes according to gases. Since MEMS metal oxide semiconductor gas sensors are particularly sensitive to poisoning and are required small in size, substituted polyacetylenes can be suitably used for the prevention of poisoning instead of adsorbent filters. MEMS metal oxide semiconductor gas sensors can be implemented in smartphones and be applied for the monitoring of VOC in the environment. In this application, substituted polyacetylenes are well fit to MEMS metal oxide semiconductor gas sensors, since they permeate toluene and do not substantially permeate cyclo-siloxanes.

Substituted polyacetylenes are more oleophilic than TEFLON AF (a registered trademark) and permeate acetone, acetaldehyde, methyl mercaptan in preference to water vapor. While exhaled air contains a large volume of water vapor, substituted polyacetylenes can restrict the permeation of water vapor. When the above compounds in human exhaled air are detected at a low concentration, rapid testing of metabolism, diabetes, and oral cavities can be performed. While electrochemical gas sensors are less affected by water vapor, they are not suitable at low concentrations for detecting acetone in exhaled air.

Preferably, the gas detector further comprises an adsorption filter configured to adsorb gasses different from one to be detected and having permeated the gas separation membrane. In this case, substituted polyacetylene forms a pre-filter of the adsorption filter, and the combination of the substituted polyacetylene and the adsorption filter block unnecessary gases. For example, when detecting methane selectively from ethanol, it is preferable to provide an adsorption filter comprising activated charcoal, silica gel, zeolite, or the like for adsorbing ethanol at a downstream side of the gas separation membrane (a position nearer to the sensing element). When stylene, pinene, or the like works as catalyst poison, it is preferable to use the combination of substituted polyacetylene and an adsorption filter such as activated charcoal or silica gel to remove stylene and pinene by the adsorption filter.

Particularly preferably, the gas separation membrane covers the outside of the adsorption filter. Then, the combination of the gas separation membrane and the adsorption filter can be implemented compactly.

FEATURES FOR CARRYING OUT THE INVENTION

The best embodiment and other embodiment for carrying out the invention will be described.

Figure 1:
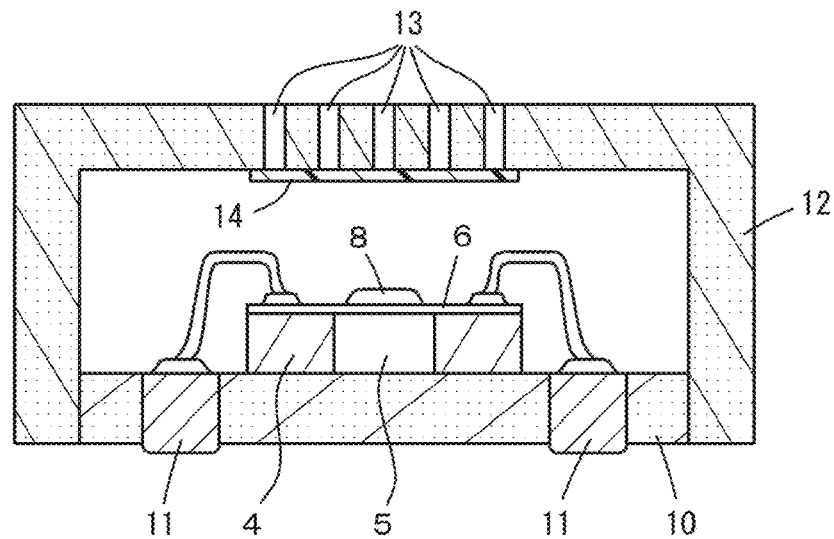
FIG. 1 A sectional view of the gas sensor according to a first embodiment

FIG. 1 indicates an embodiment of a MEMS gas sensor. Indicated by 2 is the gas sensor. A Si chip 4 (sensing element) is provided with a cavity 5 that is covered by a support membrane 6. A metal oxide semiconductor membrane 8 of $SnO_2$, $WO_3$, and so on, is provided on the support membrane 6, and its resistivity changes when in contact with gases. The support membrane 6 further has a heater and electrodes not shown in the figure. The gas sensor 2 is further provided with a base 10, a cover 12 comprising ceramics, plastic, metal, or the like. The Si chip 4 is electrically connected to the outside through lead wires and metalized portions 11.

The cover 12 is air-permeable, is provided with a vent hole 13, for example, at the top position, and is provided with a gas separation membrane 14 comprising a substituted polyacetylene (substituted polyacetylene membrane) on the vent hole 13, namely on the side facing the Si chip 4. Preferably, the substituted polyacetylene membrane 14 comprises PMP, PDPA, or the like, which does not include hetero-atom such as Si, or Ge, since there is no possibility of contamination by the hetero-atom. Since substituted polyacetylene membranes 14 have generally high air-permeability, a thick membrane 14 of them, 10 to 50 micrometer in thickness and as a monolayer membrane without a support layer, is fixed on the inner top portion of the cover 12.

Among gas components in the periphery, poisoning substances such as cyclo-siloxanes have too large molecular sizes to permeate the substituted polyacetylene membrane 14. On the contrary, molecules having a molecular size from hydrogen to toluene permeate the substituted polyacetylene membrane 14 and are detected by the Si chip 4. Therefore, the gas sensor 2 can detect VOC.

The metal oxide semiconductor membrane 8 is sometimes affected by highly humid atmospheres when placed therein for a long period. However, the substituted polyacetylene membrane 14 is oleophilic, allows only slow permeation of water vapor, and thus relaxes the influence of humid atmospheres. Detection of acetone, acetaldehyde, methyl-mercaptan, and so on, in exhaled air enables a rapid test for metabolism and health conditions. Since the substituted polyacetylene membrane 14 has a low water vapor permeation rate, the detection of these substances in exhaled air becomes easier. Further, the substituted polyacetylene membrane 14 has a higher permeability for acetone than for ethanol, and therefore, the detection of acetone becomes easier.

Figure 2:
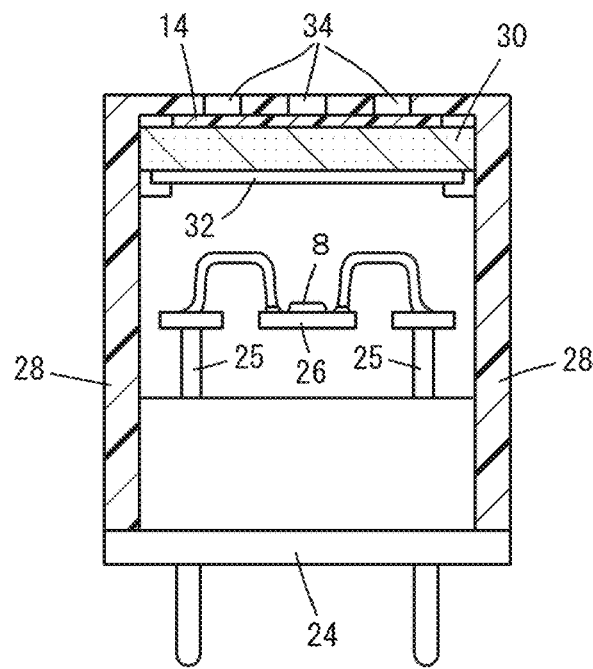
FIG. 2 A partially sectional view of the gas sensor according to a second embodiment FIG. 3 A schematic plan view of a gas detector provided with a gas separation membrane in the gas flow path FIG. 4 A characteristic view of response to $CH_4$ before and after siloxane exposure FIG. 5 A characteristic view of response to $H_2$ before and after siloxane exposure

FIG. 2 indicates another embodiment where the substituted polyacetylene membrane 14, similar to that in the previous embodiment, is provided as a pre-filter of an adsorption filter 30 in a conventional gas sensor. A substrate 26 is provided over a base 24 comprising ceramic, plastic, or the like and is supported by pins 25. The substrate 26 is provided with a heater and electrodes, which are not shown in the figure, and supports the metal oxide semiconductor membrane 8, similar to that in the previous embodiment.

The gas sensor is provided with a cover 28 comprising plastic, ceramic, metal, or the like, and on the top inner face of the cover 28, the substituted polyacetylene membrane 14, the adsorption filter 30, and a porous film 32 are laminated. Indicated by 34 is vent holes, which are not needed when the material of the cover 28 is air-permeable. The substituted polyacetylene membrane 14 blocks cyclo-siloxanes and so on, and works as the outside cover of the adsorption filter 30. The adsorption filter 30 comprises activated charcoal, silica gel, zeolite, and so on, and has a seat-like form, for example, but can be granular. The adsorption filter 30 adsorbs gases such as ethanol and adsorbs and eliminates poisonous substances when poisonous substances are not fully blocked by the substituted polyacetylene membrane 14. The porous film 32 is an inner cover of the adsorption filter 30, supports the filter 30, and blocks fine powders from the filter 30.

In FIGS. 1 and 2, the substituted polyacetylene membrane 14 is provided in metal oxide semiconductor gas sensors. However, the substituted polyacetylene membrane 14 is also usable as a filter in an electrochemical gas sensor or a contact combustion gas sensor.

Figure 3:
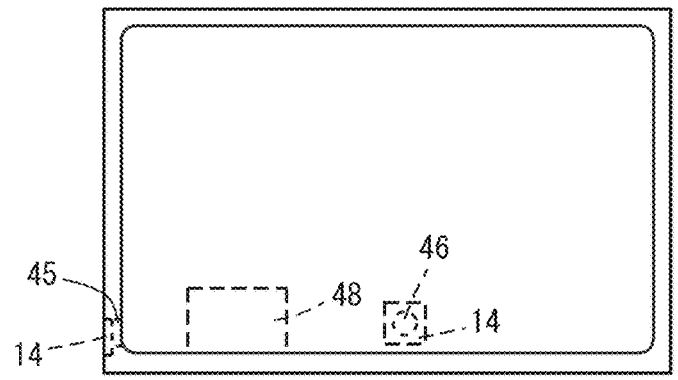

FIG. 3 indicates a gas detector comprising a smartphone implemented with a gas sensor 48. The gas inlet 45 and gas outlet 46 of the smartphone 42 are covered by the substituted polyacetylene membranes 14, similar to that of the embodiment in FIG. 1 so that the gas sensor 48 is protected from poisonous substances. When the gas sensor 48 is used for the analysis of exhaled air, the substituted polyacetylene membranes 14 restrict the permeation of water vapor and make the detection of acetone, acetaldehyde, methyl mercaptan, or the like, easier.

Durability Test against Siloxanes

Figure 4:
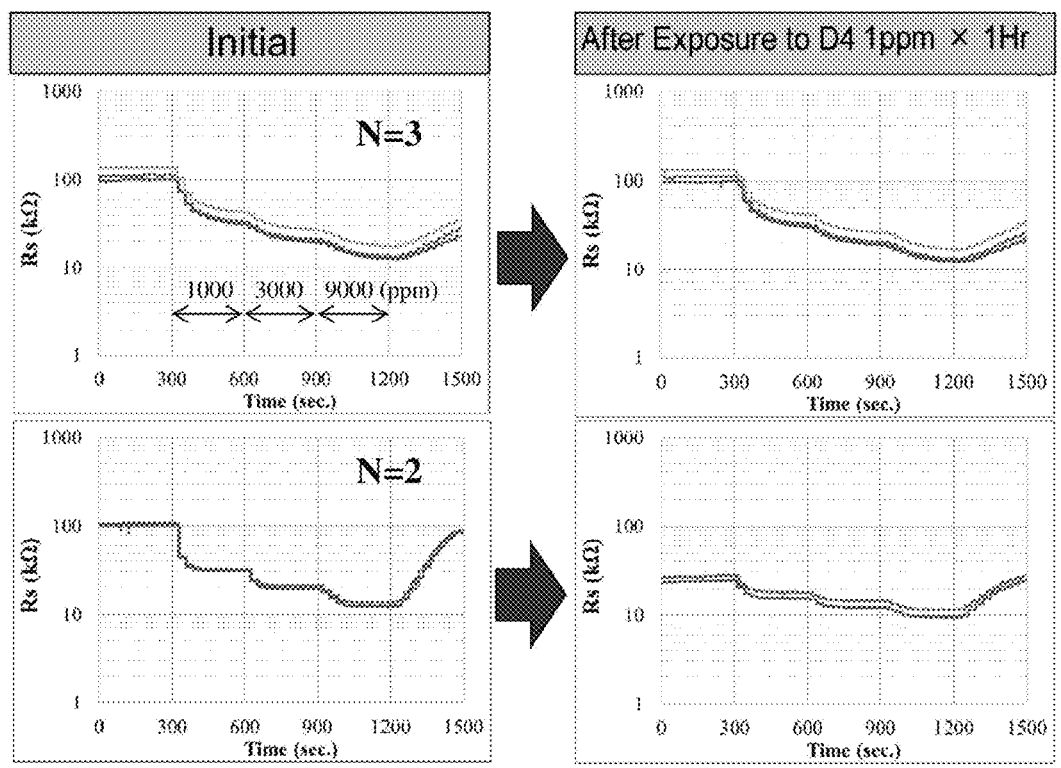
Figure 5:
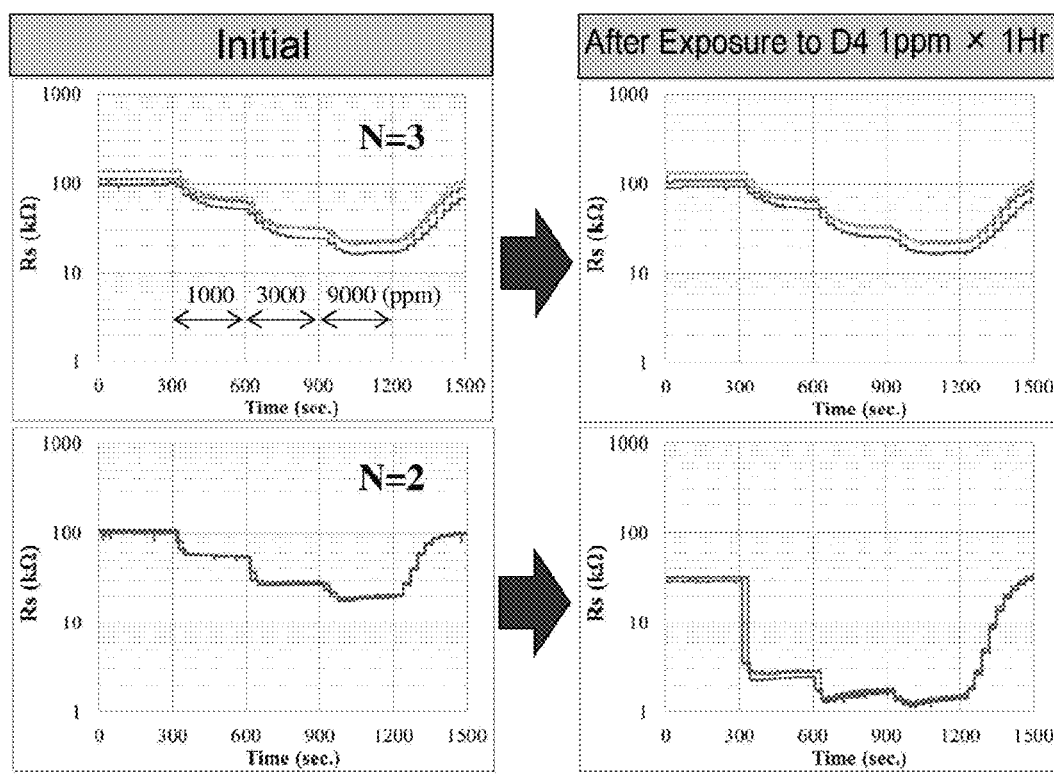

The responses of gas sensor 2 to $CH_4$ and $H_2$ were observed before and after exposure to one ppm of a cyclo-siloxane (D4). The metal oxide semiconductor membrane 8 in the gas sensor 2 was a $SnO_2$ membrane having a thickness of 40 micrometer, and the operating condition was intermittent heating to heating for 0.1 second to the maximum heating temperature of 430 degree Celsius once every 30 seconds. A load resistor was connected to the gas sensor 2, and the resistance of the metal oxide semiconductor membrane 8 was measured at the end of heating. The gas separation membrane 14 comprised a PTMSDPA membrane having a thickness of about 10 micrometer laminated on a porous PTFE membrane. The gas sensors of embodiment had the gas separation membrane 14, and comparative gas sensors had a simple porous PTFE membrane instead of the gas separation membrane 14. The number of the gas sensors was three for the embodiment and 2 for the comparative example. The detected gases were $CH_4$ (FIG. 4) and $H_2$ (FIG. 5), and their concentration was from 1000 to 9000 ppm. The upper portions in FIGS. 4 and 5 indicate the result in the embodiment and the lower portions indicate those in the comparative example. FIGS. 4 and 5 indicate the gas separation membrane 14 reduces the influence of siloxanes.

Supplements

Polyacetylene membranes have large free volumes and are oleophilic among gas selective permeable membranes. Regarding the gas selectivity of the polyacetylene membranes, the following two mechanisms are reasonable:

selectivity according to the relative sizes of gases to the pore size, and selectivity according to the solubility of gas molecules in the membrane and diffusion velocities of dissolved gas molecules. The mechanism due to the pore size utilizes that molecules larger than the pore size can not enter into the pores. The mechanism due to the solubility and so on utilizes that large size molecules are trapped within relatively large pores after resolving in the membrane and are difficult to permeate outside of the membrane. The inventors speculate, in substituted polyacetylene membranes, both factors of the selectivity according to the size differences between the pores and siloxane molecules and the slow diffusion of siloxane molecules dissolved in the membrane. In substituted polyacetylene membranes, small gas molecules are not trapped in the pores, permeate promptly through the membrane, and are detected promptly.

LIST OF SYMBOLS 2, 22 gas sensor
4 Si chip
5 cavity
6 support membrane
8 metal oxide semiconductor membrane
10, 24 base
11 metalized portion
12, 28 cover
13, 34 vent hole
14 gas separation membrane
25 pin
26 substrate
30 adsorption filter
32 porous film
42 smartphone
45 gas inlet
46 gas outlet
48 gas sensor

What is claimed is:

1. A gas detector comprising:
   a gas separation membrane comprising substituted polyacetylene where a substituent group is combined to a double-bonded carbon atom in backbone chain of the substituted polyacetylene; and
   a sensing element configured to detect gas permeated through the gas separation membrane,
   wherein the sensing element is a metal oxide semiconductor type or a contact combustion type, and
   wherein the gas separation membrane is configured to block cyclo-siloxanes and to permeate gas to be detected.

2. The gas detector according to claim 1, wherein the gas separation membrane is a monolayer membrane without a support layer.

3. The gas detector according to claim 1, wherein the sensing element comprises a MEMS chip supporting a metal oxide semiconductor membrane whose resistance changes according to gases.

4. The gas detector according to claim 1, wherein the gas separation membrane is configured to block water vapor in human's exhaled air.

5. The gas detector according to claim 1, wherein the gas separation membrane is configured to detect VOC (volatile organic compounds) in environmental atmosphere.

6. The gas detector according to claim 1, wherein the gas detector further comprises an adsorption filter configured to adsorb gases different from one to be detected and having permeated the gas separation membrane.

7. The gas detector according to claim 6, wherein the gas separation membrane covers the outside of the adsorption filter.

8. The gas detector according to claim 6, wherein the gas to be detected is methane and wherein said adsorption filter is configured to adsorb ethanol, stylene, and pinene.

* * * * *